United States Patent

Hedlund et al.

Patent Number: 5,407,438
Date of Patent: Apr. 18, 1995

[54] CASING FOR AN ABSORBENT ARTICLE

[75] Inventors: Gunilla Hedlund, Ljungskile; Ing-Britt Magnusson, Mölnlycke, both of Sweden

[73] Assignee: Molnlycke AB, Gothenburg, Sweden

[21] Appl. No.: 50,388

[22] PCT Filed: Nov. 26, 1991

[86] PCT No.: PCT/SE91/00802
  § 371 Date: May 11, 1993
  § 102(e) Date: May 11, 1993

[87] PCT Pub. No.: WO92/09253
  PCT Pub. Date: Jun. 11, 1992

[30] Foreign Application Priority Data

Nov. 27, 1990 [SE] Sweden .................................. 9003773

[51] Int. Cl.6 ..................... A61F 13/15; A61F 13/20
[52] U.S. Cl. ....................... 604/385.2; 604/358; 604/369; 604/373; 604/385.1; 604/393
[58] Field of Search ............ 604/358, 373, 369, 385.1, 604/385.2, 386, 387, 389, 390, 391, 392, 393, 394, 397, 398

[56] References Cited

U.S. PATENT DOCUMENTS

| | | | |
|---|---|---|---|
| 2,545,674 | 3/1951 | Ralph | 604/394 |
| 3,400,718 | 9/1968 | Saijo | 604/394 |
| 4,753,646 | 6/1988 | Enloe | 604/389 |

FOREIGN PATENT DOCUMENTS 0219326  4/1987  European Pat. Off. .
182446   2/1963  Sweden .

Primary Examiner—Randall L. Green
Assistant Examiner—P. Zuttarelli
Attorney, Agent, or Firm—Young & Thompson

[57] ABSTRACT

The present invention relates to a casing intended for an absorbent article, such as a disposable diaper, incontinence guard or like article. The casing (1) includes a front-part (5), a rear-part (10) and an intermediate crotch-part (22) made of flexible casing material. According to the invention, an elastic band (14, 15) is provided on each outer edge of the casing sides, at least within the crotch-part of the casing. The elastic band is attached, in a stretched state, to that side of the casing which lies nearest the skin of the user when the absorbent article is worn, by means of a narrow, elongated join. The elastic bands also include parts which extend transversely in relation to respective joins, in a direction from the joins in towards the central part of the casing.

9 Claims, 2 Drawing Sheets

CASING FOR AN ABSORBENT ARTICLE

FIELD OF THE INVENTION

The present invention relates to a casing for an absorbent article, such as a disposable diaper, incontinence guard or like article.

BACKGROUND OF THE INVENTION

Such casing normally include leg elastication which, when the article is worn, embrace the wearer's thighs so as to prevent the occurrence of gaps between the article and the wearer's thighs and therewith provide a seal against lateral leakage. The leg elastication will often consist of elastic threads or elastic bands which are enclosed between the two layers or sheets from which such casings are normally made. It is also known to use elastic devices in so-called all-in-one diapers which function to gather together those side-parts of the casing material which lie outside the absorbent pad in a manner to lift these parts in at least the crotch-part of the article, so as to form barriers against lateral leakage. Although this design will normally function in the manner intended, there is a danger of the upstanding side part of the casing being folded inwards over the absorbent pad when the diaper is placed in position on the wearer. Further, when narrow elastic threads are used, there is a danger of the threads chaffing against the wearer's skin.

SUMMARY OF THE INVENTION

One object of the present invention is to provide a casing for an absorbent article having leg elastication which, in addition to satisfying the demands normally placed on such articles, will also form a barrier which prevents lateral leakage of liquid and which will also afford a high degree of comfort to the wearer of the absorbent article without risk of chaffing of the skin, and which will enable the absorbent article to be readily positioned correctly on the wearer.

According to the present invention, this object is achieved with a casing for an absorbent article, such as a disposable diaper, incontinence guard or like article comprising a front-part, a rear-part and an intermediate crotch-part of flexible casing material, which casing is characterized in that an elastic band is disposed on each outer edge of the casing sides, at least within the crotch-part; in that the elastic band is attached in a stretched or tensioned state to that side of the casing which lies nearest the wearer's skin in use by means of respective narrow, longitudinally extending joins; and in that the elastic band includes parts which extend transversely on relation to respective joins, in a direction away from said joins and in towards the central part of the casing. The narrow joins function as a hinge about which the elastic band can swing freely, therewith facilitating correct positioning of the absorbent article of which the casing forms part. Since the elastic band is manufactured separately from the casing, the band can be made from a material which is friendly to the skin and can be readily dimensioned to provide an optimum effect. Furthermore, the elastic band lies directly against the skin, which eliminates the risk that the article will become less proofed against leakage and also that the skin will not be subjected to the chaffing that folds of casing material between skin and elastic threads of conventional leg elastication can cause. Because the manner in which the elastic band is connected to the legs in the crotch-part of the article enables the band to pivot around the joins to a substantially vertical position, those parts of the elastic band that are swung away from the joins will function as liquid barriers. When the inventive casing is intended for repeated use and is therewith intended to coact with loose absorbent, disposable pads, the elastic bands will assist in holding the absorbent pad in position in the casing.

BRIEF DESCRIPTION OF THE DRAWINGS

These and other features of the invention, and advantages afforded thereby, will be apparent from the following description of a preferred embodiment of the invention, made with reference to the accompanying drawings, in which.

DETAILED DESCRIPTION OF THE INVENTION

Figure 1:
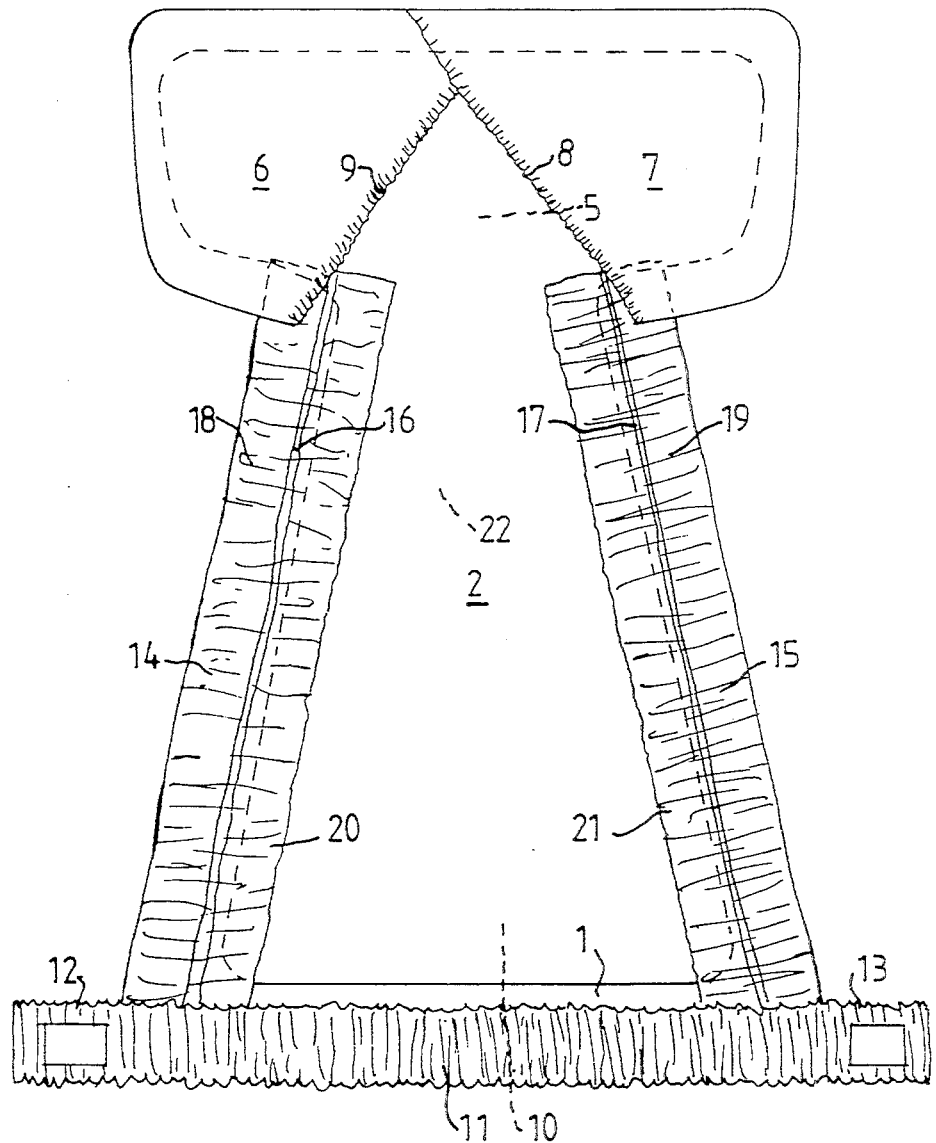
FIG. 1 illustrates from above an absorbent article provided with an inventive casing, wherein that side of the casing which lies nearest the wearer's skin in use faces towards the viewer.

The absorbent article illustrated in the drawings comprises a T-shaped casing 1, in which a T-shaped absorbent pad 2 is placed. The casing 1 is intended for repeated use, whereas the pad 2 is intended for one-time-use only. The casing 1 is preferably made substantially of skin-friendly, liquid-impermeable but air-permeable material, and the absorbent pad is preferably comprised of a core 3 of absorbent material surrounded by an insulating layer 4 of good liquid-permeability. This combination of casing and absorbent-pad material is suitable when the absorbent pad, as seen structurally, is homogenous or has a symmetrical structure in relation to a central transverse plane, such as to make no difference how the absorbent pad is turned when placed in the casing. In other cases, the insulating layer 4 of the absorbent pad should have an appearance which is pronouncedly different from the appearance of the layer surrounding the underside of the absorbent pad, said insulating layer 4 then extending solely on the upper side of the pad. It will be understood that, to a certain extent, the choice of casing material is dependent on the design of the absorbent pad 2. For example, it is not necessary for the casing material to be impervious to liquid when the layer surrounding the underside of the absorbent pad is itself impervious to liquid and extends beyond the edges of the absorbent core. It will therefore be obvious that the invention is not restricted to the aforesaid choice of casing material and that the casing can be made from any appropriate type of material when practicing the present invention. The casing may also comprise two or more layers of mutually different materials.

Although not necessary, the illustrated parts 6, 7 of the front casing part 5 will also preferably include liquid-permeable materials which, as illustrated in FIG. 1, are disposed on top of the T-shaped layer from which the casing 1 is essentially constructed, in the laterally extending parts of the T, and fastened along the outer edges of these parts on the inside of the casing, i.e. on the side of the casing facing towards the viewer. The parts 6, 7 form together with said laterally extending parts of the T-shaped casing material pockets which function to hold firm the T-shaped part of an absorbent pad 2 inserted in the casing 1. Elastic threads or bands 8, 9 are provided along the edges of the pocket openings.

Provided along the edge of the rear-part 10 of the casing 1 is a waist elastic 11 in the form of an elastic band which extends beyond the side edges of the casing 1, so as to form elastic fastener tabs 12, 13 which are intended to be fastened to the outside of the front casing part, so as to impart a trouser-like configuration to the article when fitted for wear. The tabs 12, 13 include, in a conventional manner, means which enable the tabs to be fastened to the outer surface of the front casing part. Examples of such fastening means include self-gripping devices (Velcro-fasteners), snaps (press studs) and adhesive means.

Broad elastic bands 14, 15 extend along the side edges of the casing 1, from the rear casing pert over the crotch-part 22 and slightly inwards on the front casing part 5. The elastic bands 14, 15 are fastened in a stretched state to respective side edges of the casing 1 by means of respective narrow, elongated joins 16 and 17, said joins either being in the form of welded seams or in the form of an adhesive join. It is also conceivable to sew the bands 14, 15 onto said side edges. The elastic bands 14, 15 include respective transverse parts 18, 20 and 19, 21, which extend transversely on both sides of the respective joins 16 and 17. In the case of the described embodiment, the elastic bands 14, 15 and the waist elastication comprise foamed elastic material enclosed in a casing of skin-friendly, heat-meltable nonwoven fabric. Those parts of the nonwoven fabric which extend on opposite sides of the elastic band are connected together punctilinearly through openings provided in the foamed material. Naturally, other elastic material can be used, such as rubber, instead of the elastic foamed material, and neither is it necessary to surround the elastic band with casing material. However, that side of the elastic band which faces the wearer will preferably be coated with a soft, skin-friendly material when the band is not manufactured from material which possesses these properties.

Figure 2:
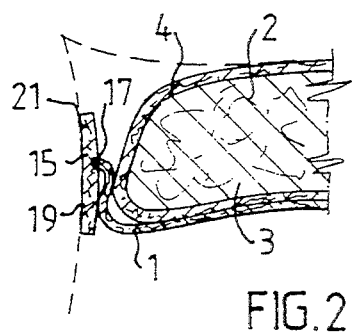
FIG. 2 is a cross-sectional view of part of the crotch region of the article shown in FIG. 1, with the article shown as worn.

FIG. 2 illustrates schematically a part-section of the crotch-part of the diaper shown in FIG. 1 with the diaper in its position of wear. The contours of the legs and crotch of the wearer are illustrated in broken lines. As will be seen from FIG. 2, the elastic band 15 lies tightly against the wearer's legs and adopts a practically vertical position. Because the band 15 is relatively broad, the band can be given a degree of elasticity which will ensure that the band will only be tensioned to a relatively slight extent around the wearer's legs, without jeopardizing its effectiveness against leakage. Because the tightness of the band around the wearer's legs is limited and because the band is relatively broad, the risk of chaffing against the wearer's legs is relatively small, even should the band 15 be moved relatively to the wearer's legs as the wearer moves. Because the casing can pivot freely around the joins 16, 17 relative to the elastic bands 14, 15, the risk of movement of the band as a result of leg movement is also reduced.

Furthermore, the provision of band-parts 18, 20 and 19, 21 respectively which extend transversely in relation to a longitudinally extending join facilitates correct positioning of the absorbent article on the wearer.

When the article shown in FIG. 1 is positioned for wear, the outer edges of the outer transverse parts 18, 19 of the band 14, 15 will come into contact with the wearer's legs first. The elastic bands are more rigid than the flexible casing material, which means that the upwardly directed movement (when the wearer stands up) or the upwardly-forwardly directed movement (when the wearer lies down) to which the crotch-part of the article is subjected will cause the elastic bands to pivot around the joins until the two transverse parts 18, 20 and 19, 21 of respective bands lie in abutment with the inner surfaces of the wearer's legs. This ensures correct positioning of the article.

That end of the elastic bands 14, 15 which is enclosed in the front casing part 5 is not attached to the casing 1 at its inner, transverse part 20 and 21 respectively and is therefore able to follow unhindered the upward swinging of the band around respective joins 16 and 17 initiated when putting on the article. On the other hand, the respective elastic bands 14, 15 at the rear casing part are attached to the casing through the intermediary of the waist elastic 11 included in the casing 1. Since this attachment is remote from the crotch-part of the article, it has no appreciable effect on the upward swinging of the respective elastic bands 14, 15. This manner of attachment is beneficial, because the elastic bands 14, 15 in the rear casing part positively hold the rear-part of the absorbent pad 2 to the casing 1, since upward swinging of the transverse parts 20, 21 is thereby prevented in this part.

Figure 3:
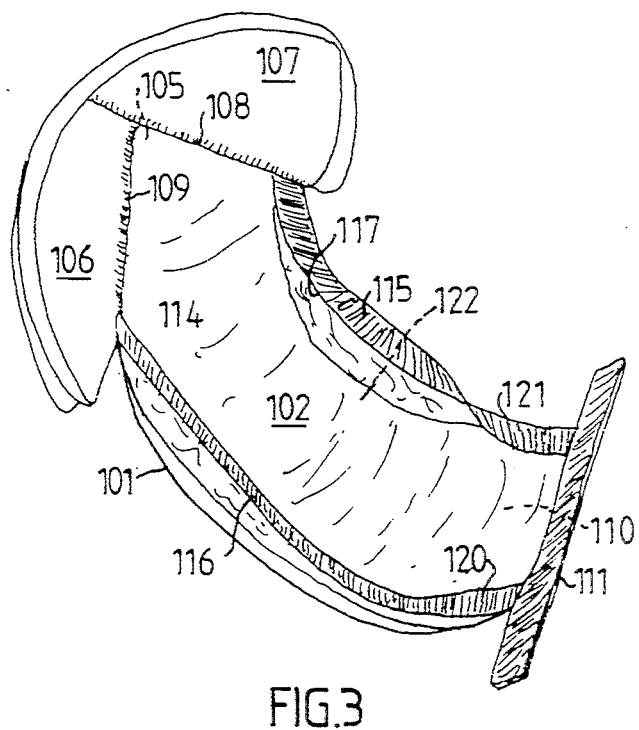
FIG. 3 is a perspective view of an absorbent article provided with another embodiment of an inventive casing.

FIG. 3 illustrates another embodiment of an inventive casing 101, which differs from the casing illustrated in FIGS. 1 and 2 in that the elastic bands 114, 115, which form the leg elastication, extend transversely in relation to the joins 116, 117 solely in towards one another and thus solely on one side of respective joins. Those component parts of the FIG. 3 embodiment which correspond to similar components of the FIG. 1 embodiment have been identified by the same reference numerals with the addition of one-hundred.

Similar to the casing one of casing 1 of the FIG. 1 embodiment, the casing 101 of the FIG. 3 embodiment coacts with an absorbent pad 102 inserted in the casing. The length of the absorbent 102 is such that the elastic bands 114,115, and therewith the casing 101, must be stretched-out in order to enable the whole of the absorbent 102 to be inserted into the casing. Subsequent to insertion of the absorbent pad, the elastic bands 114, 115 are allowed to contract so as to deform the composite article 101, 102 into the curved configuration shown schematically in FIG. 3. As indicated in FIG. 3, this contraction of the elastic bands 114, 115 will cause the parts of the casing 101 located in the crotch-part laterally outside the absorbent pad 102 to lift. The elastic bands 114, 115 will also be lifted to form the desired liquid barriers. The elastic bands of this embodiment will also lie directly against the legs of the wearer, and consequently there is no risk that folds of casing material will lie between the wearer's legs and the leg elastic.

In one variant of this embodiment, the elastic bands 114, 115 are also fastened to the casing 101 at the front edge thereof, more specifically to the material 106, 107.

As will be understood, the inventive casing can also be used for all-in-one diapers. In this case, the elastic bands which form the leg elastication are attached along the edge of the casing layer which encloses the absorbent pad and on the side of said casing layer which lies nearest the wearer's skin in use. In this application, said elastic bands may include transverse parts on both sides of the narrow joins, or alternatively only on those sides of the joins which face towards one another.

In the case of the illustrated embodiments, the joins between the elastic bands forming said leg elastication are disposed on the outer edges of respective casings. It is conceivable, however, to extend the casing material beyond the joins so that when the elastic bands are swung upwards, the casing material will be folded downwards and therewith not disturb the function of the elastic bands. For aesthetic reasons, however, it is preferred to form the joins precisely at the outermost edge of the casing. In the case of the illustrated embodiments, the parts of the elastic bands extending transversely relatively to the joins are of mutually equal lengths, although it is, of course, possible to vary the size of these transverse parts, either by varying the width of the elastic bands in their length directions, or by placing an elastic band of uniform width obliquely in relation to the outer edge. Neither need the longitudinally extending joins be straight along the whole of their extension, since they need only be straight within the crotch region of the article in order to form a hinge. Consequently, the elastic bands may also conform, to some extent, to the contours of the casing with non-straight parts, if so desired.

We claim:

1. A casing for an absorbent article intended to be worn by a person, said casing comprising a front-part, a rear-part, a central part, casing sides, and an intermediate crotch-part made of flexible casing material, a unitary and integral elastic band provided on each outer edge of the casing sides, at least within the crotch-part; said elastic band being attached in a stretched state to that side of the casing which lies against a wearer's skin when the absorbent article is worn by a narrow, elongated join; said elastic band including parts which extend transversely in relation to the respective joins in a direction extending from said joins in towards the central part of the casing, and said parts, when the article is in use, constituting leg elastics, as well as upstanding barriers preventing lateral leakage of liquid.

2. A casing according to claim 1, wherein the elastic bands include transversely extending parts on both sides of respective joins.

3. A casing according to claim 2, wherein the elastic bands have a greater rigidity than the casing material.

4. A casing according to claim 1, wherein the elastic bands are made from an elastic, foamed material which is provided with a skin-friendly material at least on that side of the elastic band which lies nearest to the wearer's skin when the article is in use.

5. A casing according to claim 4, wherein the foamed material is enclosed in and connected with a casing of heat weldable material; and the joins between respective elastic bands and casing material have the form of welded seams.

6. A casing according to claim 1, wherein the elastic bands extend from the rear-part slightly inwards on the front-part; and a rear end of each elastic band is connected to the casing.

7. A casing according to claim 6, wherein a forward end of each elastic band is connected to the casing.

8. A casing according to claim 1, further including means for releasably holding a disposable absorbent pad which is adapted to be inserted into the casing.

9. A casing according to claim 1, wherein the casing includes two casing layers between which an absorbent pad is enclosed.

* * * * *